United States Patent [19]

Becker et al.

[11] Patent Number: 5,041,377
[45] Date of Patent: Aug. 20, 1991

[54] SUBTILISIN CRYSTALLIZATION PROCESS

[75] Inventors: Todd Becker, Burlingame; Virgil B. Lawlis, Jr., San Mateo, both of Calif.

[73] Assignee: Genencor International Inc., South San Francisco, Calif.

[21] Appl. No.: 611,967

[22] Filed: Nov. 13, 1990

Related U.S. Application Data

[63] Continuation of Ser. No. 538,597, Jun. 13, 1990, which is a continuation of Ser. No. 169,990, Mar. 18, 1988, abandoned.

[51] Int. Cl.$^5$ .......................... C12N 9/00; C12N 9/50; C12N 9/98; C12N 1/20
[52] U.S. Cl. .................................. 435/220; 435/187; 435/188; 435/219; 435/221; 435/272; 435/252.5; 435/803; 435/814; 435/816; 435/832; 435/839
[58] Field of Search ............... 435/222, 221, 219, 187, 435/188, 252.5, 832, 839, 814, 803, 816

[56] References Cited

U.S. PATENT DOCUMENTS

| | | | |
|---|---|---|---|
| 3,858,854 | 1/1975 | Win et al. | 435/187 |
| 4,016,040 | 4/1977 | Win et al. | 435/188 |
| 4,262,092 | 4/1981 | Bauer | 435/280 |
| 4,480,037 | 10/1984 | Ichishima et al. | 435/832 |
| 4,764,470 | 8/1988 | Durham et al. | 435/221 |

OTHER PUBLICATIONS

Bryan et al., *Chemical Abstracts*, 107: 171427b (1987) "Proteases of Enhanced Solubility: Characterization of Thermostable Variant of Subtilisin".
Toyo Soda Manufacturing Company Ltd., *Chemical Abstracts*, 97:2861h (1982) "Saturated Enzyme Solutions".
Albert L. Lehninger, *Biochemistry, First Edition, N.Y.: Worth Publishers, Inc., 1970, pp. 133-134*.
Northrup et al., *Crystalline Enzymes*, (1948) Columbia Vine Press, New York, N.Y., pp. 253-254.
Tauber et al., *Chemistry and Technology of Enzymes*, (1949) Wiley and Sons, New York, N.Y., pp. 137-140.
Scopes, Robert K., "Crystallization of Proteins", *Protein Purification: Principles and Practice*, Second Edition, New York, Springer-Verlag, 1987, pp. 296-299, and pp. 256-259.
Lehninger, Albert L., "Separation Procedures Based on Solubility Differences", *Biochemistry*, Second Edition, N.Y., Worth Publishers, Inc., 1975, pp. 160-163.
Gilliland, et al., "Crystallization and Preliminary X-ray Defraction Studies of Subtilisin GX from *bacillus* SP. GX 6644", *The Journal of Biological Chemistry*, (1987) vol. 262, No. 9, pp. 4280-4283.
Chandrasekaran et al., "Purification of Subtilisin by Single Step Affinity Chromotography", *Analytical Biochemistry*, 150, pp. 141-144 (1985).

Primary Examiner—Johnnie, R. Brown
Assistant Examiner—Pamela S. Webber
Attorney, Agent, or Firm—Burns, Doane, Swecker & Mathis

[57] ABSTRACT

Crystalline subtilisin is produced by adding a halide salt, such as sodium chloride or calcium chloride, to a concentrated subtilisin solution (at least about 40 g/l). This process does not produce amorphous subtilisin even at high salt concentrations in the solution. Optionally, subtilisin seed crystals also may be added to the concentrate to speed up the crystallization process.

20 Claims, 3 Drawing Sheets

SUBTILISIN CRYSTALLIZATION PROCESS

RELATED APPLICATION

This application is a continuation of Ser. No. 07/538,597 filed June 13, 1990, which is a continuation of Ser. No. 07/169,990 filed Mar. 18, 1988, now abandoned.

FIELD OF THE INVENTION

The present invention relates to enzyme recovery and purification and, more particularly, to a process for purification of subtilisin by crystallization.

BACKGROUND OF THE INVENTION

Subtilisin is a protease having a wide range of applications including use in laundry detergents, silver recovery, manufacturing of fish meal and other products and processes. The crystalline form of subtilisin is preferred for a number of reasons. Crystalline subtilisin is of higher purity than other forms of subtilisin produced by other routes, such as precipitation of amorphous subtilisin. Subtilisin crystals afford a high degree of stability as well as flexibility in choices of media and formulation for various desired end uses. Subtilisin, whether in crystalline or in precipitated amorphous form, can be dried and used in various granular or powdered products. However, it is more often dissolved and formulated in the form of various liquid products, e.g., in aqueous, glycerin, sorbitol, propylene glycol, etc., solutions, for use in liquid products or for use in manufacturing of liquid or solid products. Because of its higher purity, crystalline subtilisin and liquid products made from the crystalline form have a number of high grade uses, such as in medical applications and in food grade products.

The subtilisin crystals themselves are rhomboidal plates usually ranging in size from about 5 to about 50 microns. The crystals have a solubility of about 4 grams per liter(g/l) in water, about 8 g/l in brine, and over about 500 g/l in propylene glycol.

Subtilisin crystals have been obtained from fermentation of *Bacillus subtilis* in much the same way as crystals of other enzymes are obtained from given fermentations. A fermentation mixture is first subjected to a separation step which removes bacterial cells and suspended solids to form a resulting solution or broth free of solids. The resulting solution is often concentrated to provide a certain minimum concentration level of the desired enzyme. Crystallization is then carried out, usually with the aid of seed crystals, and the high purity crystalline product separated from the solution.

As discussed in "Preparation And Crystallization Of The Enzymes," from Northrup, et al., *Crystalline Enzymes*, (1948) Columbia Vine Press, New York, New York, at pp. 253-254, concentrated protein solutions, i.e., 1-10 percent, are essential to protein crystal production, because proteins in dilute protein solutions can be separated only with difficulty, if at all, whereas the same proteins in concentrated solution are typically much easier to separate. It is also necessary to crystallize the protein without forming precipitates which result in the less pure amorphous form. The crystallization is induced by adjusting the relative concentrations of protein, salt, solvent and/or organic solvents in the solution. It is important that the solution not be saturated or too highly supersaturated in salt or solvent since supersaturation favors the formation of the less desirable amorphous form of the protein by precipitation. Therefore, an optimal condition for obtaining a crystalline enzyme product has been a concentrated salt/enzyme solution at the level of very slight subsaturation.

Such optimal conditions of slight supersaturation are frequently difficult to achieve and particularly difficult to maintain during processing using conventional crystallization techniques. More specifically, the usual procedure for crystallization of enzymes involves adding a precipitating agent, such as ammonium sulfate or sodium sulfate, until a precipitate just appears. However, a precipitate frequently does not appear until the solution is too highly supersaturated and thus, the process has always involved a risk that the amorphous form of the enzyme would be produced by precipitation.

Even in instances where the optimal slight supersaturation is achieved, such ideal conditions rapidly become non-ideal. More specifically, by removing protein from solution as the crystals form, the remaining solution loses its near saturation concentration and it becomes increasingly difficult for more crystals to form. This leads to considerable losses of protein product since much of the protein may be left behind in the supernatant. To overcome this problem, it is necessary to continually adjust the solution conditions by adding additional amounts of salts such that the solution can be kept in a slightly supersaturated state until nearly all the protein has crystallized therefrom.

As is apparent from the above discussion, currently known techniques for the preparation of crystalline subtilisin are often unreliable and difficult to control. Not only must the practitioner be able to determine the point at which a subtilisin solution is slightly supersaturated but once crystallization commences, such practitioner must also continually adjust the solution system to maintain the desired concentration to avoid loss of the valuable subtilisin product and to avoid any too highly supersaturated conditions and the consequent formation of the amorphous form of the subtilisin.

In view of the foregoing limitations and shortcomings of known enzymatic crystallization techniques as well as other disadvantages not mentioned above, it is apparent that there is a need for a process for purifying subtilisin by crystallization which does not depend on the maintenance of a slightly supersaturated concentration of the enzyme solution for crystallization to occur and which enables efficient and reliable preparation of crystalline subtilisin. It is an object of this invention to fulfill that need by providing a process for purifying subtilisin enzyme by crystallization using salts which induce crystallization of the subtilisin enzyme when said enzyme solution is supersaturated thereby avoiding formation of the amorphous precipitates which can form when the subtilisin enzyme solution is highly supersaturated.

It is a further object of the present invention to provide a process for purifying subtilisin enzyme by crystallization which does not require ammonium sulfate as the precipitating agent, and thereby avoids the environmental and waste disposal problems attendant with ammonium sulfate use.

Another object of the present invention is to provide a process for the purification of subtilisin by crystallization which has low raw material and operating costs.

Another object of the present invention is to provide a process for the purification of subtilisin by crystallization which has the capability of high yields and high throughputs.

Another object of the present invention is to provide a process for the purification of subtilisin by crystallization which produces a subtilisin product which is of high purity and which is virtually free of microorganisms.

With the foregoing and other objects, advantages, and features of the invention that will become hereinafter apparent, the nature of the invention may be more clearly understood by reference to the following description of the invention, the appended claims and the drawings.

SUMMARY OF THE INVENTION

In one aspect, this invention provides a process for the preparation of subtilisin crystals comprising:

(i) preparing a subtilisin solution by removing cells and suspended solids from a fermentation mixture produced by fermentation of a subtilisin-producing bacterium;

(ii) forming a concentrated solution by concentrating the subtilisin solution such that the subtilisin is present in a concentration of at least about 40 g/l;

(iii) adding a halide salt in an amount effective to cause formation of subtilisin crystals; and (iv) allowing crystals of subtilisin to form.

The process of this invention provides various advantages over the prior art including certain unexpected advantages compared to the prior art processes. In addition to the advantages provided by the present invention satisfying the above stated objectives, another advantage provided by the use of the halide salts as provided in the process of this invention is that the subtilisin crystals form at the best rates when the salt/subtilisin solution is not near the saturation level. Therefore, it is not necessary (or even desirable) to maintain the concentration near or slightly above a saturated level. The present process is easy to operate and control because the salt level can be maintained and adjusted over a wider, less critical range during operation without having to keep the total solution at or near saturation.

A surprising and unexpected advantage provided by the present invention is that, contrary to prior processes, even if the halide salt/subtilisin solution becomes supersaturated, for example by addition of excess salt to the solution or by lowering the temperature of the solution, the amorphous form of the subtilisin does not appear. Surprisingly, even under salt concentrations as high as 2 M or even 4 M, only the crystalline form of subtilisin is produced, thereby providing consistently high purity crystalline subtilisin over a wide range of operating conditions.

Another advantage provided by the process of the present invention is that optimum rates of crystallization of the subtilisin usually occurs at a salt concentration far below saturation, e.g., 0.05 M to 0.6 M.

Other advantages are provided by the flexibility of the process of this invention in that the halide salt may be added to the concentrated subtilisin solution or it may be added earlier in the process to the subtilisin solution before it is concentrated. Moreover, the halide salt may be added even earlier in the process, i.e., to the fermentation mixture. This process thereby provides various options in this regard depending on the process design desired for commercial use of the process of this invention to produce crystalline subtilisin from the concentrated solution. Addition of the halide salt to the concentrated solution may be preferred in some instances for more precise control of the crystal formation. In other instances, it may be preferred to add the halide salt earlier in the process, particularly where the halide salt may have a stabilizing effect on the subtilisin being processed, which can increase the total yield of the process.

In another aspect, this invention provides a composition comprising a subtilisin solution containing a halide salt present in an amount effective to cause crystallization of subtilisin from the solution.

DETAILED DESCRIPTION OF THE INVENTION AND EMBODIMENTS THEREOF

Figure 1:
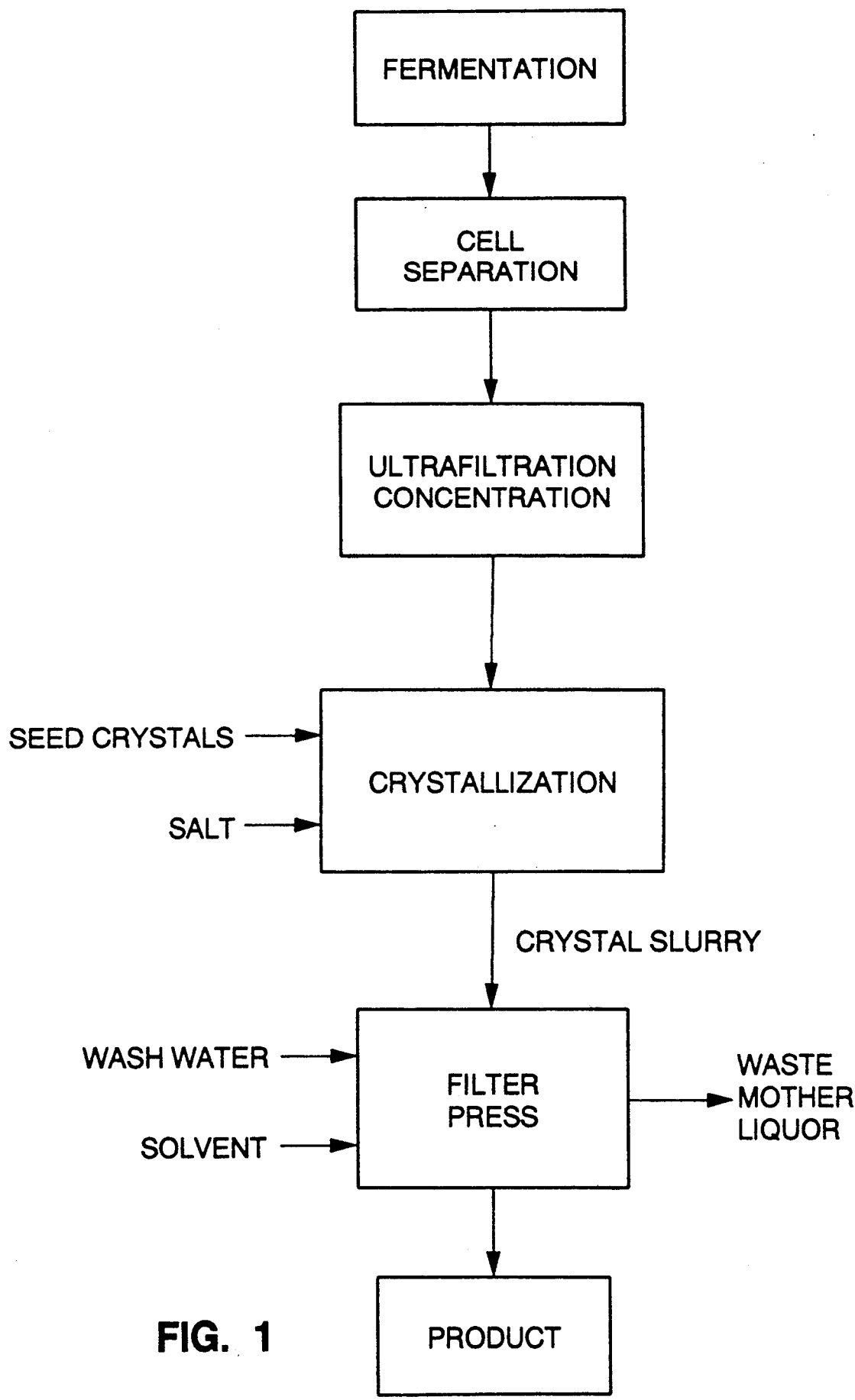
FIG. 1 is a schematic diagram of a preferred embodiment of the process of this invention.

Preparation of crystalline subtilisin according to one embodiment of the present invention is carried out by preparing a fermentation of *B. subtilis*, removing cells and suspended solids from the fermentation mixture to form a subtilisin solution, concentrating the solution such that the subtilisin enzyme is present in a concentration of at least about 40 grams per liter (g/l), adding a halide salt to the concentrated solution in an amount effective to form subtilisin crystals, and allowing crystals of subtilisin to form. This embodiment of the process of this invention is illustrated in the overall process schematically shown in FIG. 1, which shows the basic steps of fermentation of a subtilisin-producing bacterium, separation of the cells and suspended solids from the fermentation mixture, and concentration of the resulting subtilisin solution to the desired level. These fermentation, separation and concentration steps are well known in the art and conventional methods can be used in the practice thereof in connection with the practice of this embodiment of the invention. Next, in this embodiment the halide salt and seed crystals are added to perform the crystallization step to form a crystal slurry. The crystals can then be recovered by conventional filter press methods and washed to provide the desired product, which can be in dry powder or granular form or can be in the more common liquid solution form.

The fermented mixture containing cells, various suspended solids, and the desired solution of the subtilisin product, is first processed to separate such cells and suspended solids from the subtilisin solution. In this regard, conventional solid-liquid separation techniques may be employed such as filtration, centrifugation, microfiltration, rotary vacuum filtration and the like. Once the cells and solids have been separated from the solution or broth containing the dissolved subtilisin, which is usually present in a concentration of about 3 to 20 g/l, it is next necessary to concentrate the subtilisin in the solution to a concentration of at least about 40 g/l, preferably at least about 60 g/l, and more preferably to a concentration of at least about 80 g/l. Concentrations under about 40 g/l are less desirable because poor or unsatisfactory yields in crystallization usually result, while as a general rule, the process operates best and most efficiently at higher concentrations. It is preferred to use the highest concentration of subtilisin that can be achieved in the concentrated solution used in the crystallization step. However, concentrations above about 100 g/l are difficult to achieve for many subtilisin solutions; the optimum operating range for most subtilisin solutions is usually about 90 to about 100 g/l or higher when practical. Concentration of the solution may be achieved by a variety of conventional techniques including ultrafiltration, evaporation, extraction, chromatography or precipitation followed by redissolution. Selection of the concentration technique or process to be used may be influenced in part by whether the halide salt has been added according to this invention to the fermentation mixture or to the solution to be concentrated.

It has been observed that, for a given set of conditions, the amount of subtilisin remaining in the rejected mother liquor after completion of the crystallization step is decreased when higher starting concentrations of subtilisin is used in the concentrated solution fed to the crystallization step. That is, the higher the starting concentration of the subtilisin in the concentrated solution at the beginning of the crystallization, the higher will be the percent of total subtilisin recovered by crystallization, thereby providing the highest overall yields of crystalline subtilisin and the lowest losses of uncrystallized subtilisin remaining in the mother liquor. As an example, a crystalizer feed solution having a concentration of 100 g/l subtilisin will produce, after crystallization, about 22% v/v crystal solids as a slurry suspended in an equilibrium mother liquor having a concentration of about 15 g/l remaining subtilisin, which provides a maximum recovery of about 100-(100-22)(15/100), or an overall yield of 88.3%. By comparison, a feed solution having a concentration of 80 g/l subtilisin will produce about 20% v/v crystal solids in the crystallization step in an equilibrium mother liquor having a concentration of about 18 g/l remaining subtilisin, which provides a maximum recovery of about 100-(100-20)(18/80) or an overall yield of 82%.

Crystallization of subtilisin from the concentrated solution is achieved by adding an amount of a halide salt which is effective to cause the formation of subtilisin crystals. The halide salts useful in this invention include sodium chloride, calcium chloride, sodium bromide, sodium iodide, potassium chloride, potassium iodide, sodium fluoride and other halide salts and mixtures thereof which are compatible with the subtilisin being crystallized. The halide salts preferred for commercial use at present are sodium chloride and calcium chloride. The amount of halide salt effective to cause formation of subtilisin crystals will vary depending on the particular subtilisin in solution, other materials present in the solution, the concentration of the subtilisin in the solution as well as the particular halide salt or salts being used. The selection of at least an effective amount and an optimum amount of halide salt for the process of the present invention will be apparent to one skilled in the art upon consideration of these factors by following the teaching of the present invention. In general, the salt concentration should be at least about 0.01 M (10 mM), preferably from about 0.01 to about 2 M, more preferably from about 0.02 to about 1.5 M and most preferably from about 0.03 to about 1 M. Optimum ranges for some solution/salt combinations are in the range of about 0.02 to about 0.8 M, while others are in the range of about 0.1 to about 0.7 M. These amounts or concentrations of salt are equally applicable to the composition of this invention as effective to cause crystallization of subtilisin from the solution.

Without being limited by theory, it is believed that the halide salts used according to the present invention induce crystallization of subtilisin in a different manner than classical precipitants for subtilisin such as ammonium sulfate. More specifically, precipitants such as ammonium sulfate induce crystallization of the subtilisin crystals when the concentration of the solution is near saturation level. At higher levels they can lead to the precipitation of amorphous subtilisin. In contrast to classical precipitants, the halide salts used according to the present invention induce crystallization of subtilisin at a relatively low salt concentration. Moreover, as noted above, the use of halide salts according to this invention will not induce precipitation of the amorphous form of subtilisin, even at salt levels as high as 2 M or even 4 M. At very high salt concentrations, crystallization of subtilisin drops off, but only crystalline subtilisin is produced and no amorphous subtilisin is precipitated. This invention removes the risk of precipitating the amorphous form of subtilisin. As seen from the above, optimum crystallization occurs in the process of the present invention at lower salt concentrations, whereas overall yields are lower at very high salt concentrations.

Figure 2:
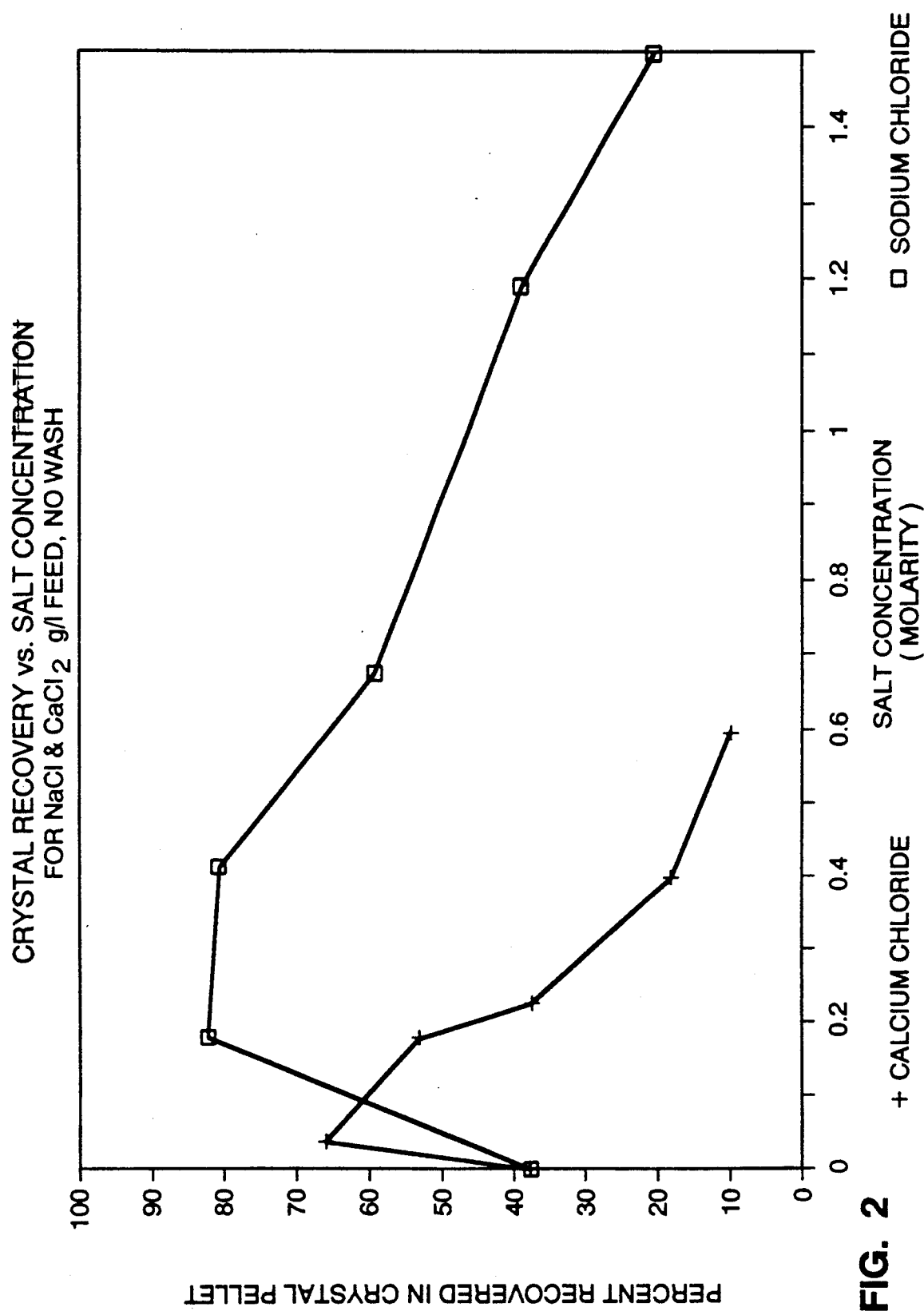
FIG. 2 is a graph depicting the percent of crystal recovery for various concentrations of sodium chloride and calcium chloride.

Whereas increasing levels of conventional precipitants can eventually cause precipitation of amorphous subtilisin precipitates, increasing the levels of the halide salts of the present invention induces increasing crystal formation up to an optimum point, followed by gradually decreasing crystal formation beyond that point. Thus, referring to FIG. 2, it can be seen that crystal recovery was maximized for sodium chloride at about 200–600 mM and for calcium chloride at about 50–200 mM which are optimum salt concentration ranges for these particular salts to provide best yield of crystallized subtilisin. The data in FIG. 2 is based on a feed from an ultrafiltration concentrate (concentrated to 80 g/l subtilisin), which was diafiltered with four volumes of deionized water to remove salts prior to addition of the halide salt and seed crystals. As can be seen in FIG. 2, sodium chloride has a higher possible yield over a wider optimum operating range and is therefore a preferred salt for the process of this invention. Beyond these optimum ranges for these particular salts, the percent recovery of crystallized subtilisin is decreased. However, the formation of amorphous precipitates of subtilisin was not observed at any concentration of these salts. The optimum concentration of sodium chloride can range between about 200 and about 600 mM and is preferably between about 400 and about 500 mM, which translates to between about 1.2% to 3.5% and preferably about 2.3% to about 2.9%, respectively. The concentration of calcium chloride can range between about 50 and about 200 mM and is preferably between about 100 and about 150 mM, which translates to between about 0.7% and about 2.9%, and preferably between about 1.5% and about 2.2%, respectively.

Although not required, subtilisin seed crystals are preferably added in an amount up to about 10% by weight, based on the weight of the solution, to promote the crystallization process. The use of seed crystals makes the kinetics of the crystallization more favorable and seems to increase overall yield of crystalline subtilisin. Nucleation may also be promoted by providing crystallization vessels having surface properties conducive to crystallization, which properties are well known by persons skilled in the art. The use of the minimum but effective amount of seed crystals for a given subtilisin solution, size of operation, process conditions, etc., will be apparent to one skilled in the art, as in conventional crystallization processes. Also, when this process is practiced as a continuous process, the crystals present in the crystallizer will act as seed crystals for fresh concentrated solution feed entering the crystallizer. Crystal growth is usually further promoted by providing gentle agitation of the crystallization vessel. One skilled in the art will also recognize that any material which may inhibit crystallization, such as propylene glycol, sodium formate, sodium sulfate, etc., should not be added to the solutions in the process of this invention until after the desired degree of crystallization has been achieved.

The temperature during crystallization should generally be between about 1° and about 10° C. and preferably, between about 3° and about 5° C. The pH at which crystallization is carried out depends on the species of the enzyme but should be in a range where the enzyme is stable, e.g., for sodium chloride and *B. amyloliquefaciens* subtilisin the pH should generally be between about 5.2 and 5.8 and preferably between 5.3 and 5.6. At pH levels below about 5.2 or above about 5.8, the subtilisin may be unstable. The amount of time required for the crystallization process to go to substantial completion or to the desired equilibrium, of course, depends not only on the various process conditions but also on whether or not seed crystals are used. Where seed crystals are not employed, about 48 hours are typically required to reach equilibrium, which corresponds to a remaining subtilisin concentration in the solution below about 20 g/l. Where seed crystals are employed, the time is typically reduced to less than about 18 hours to reach the same equilibrium.

Figure 3:
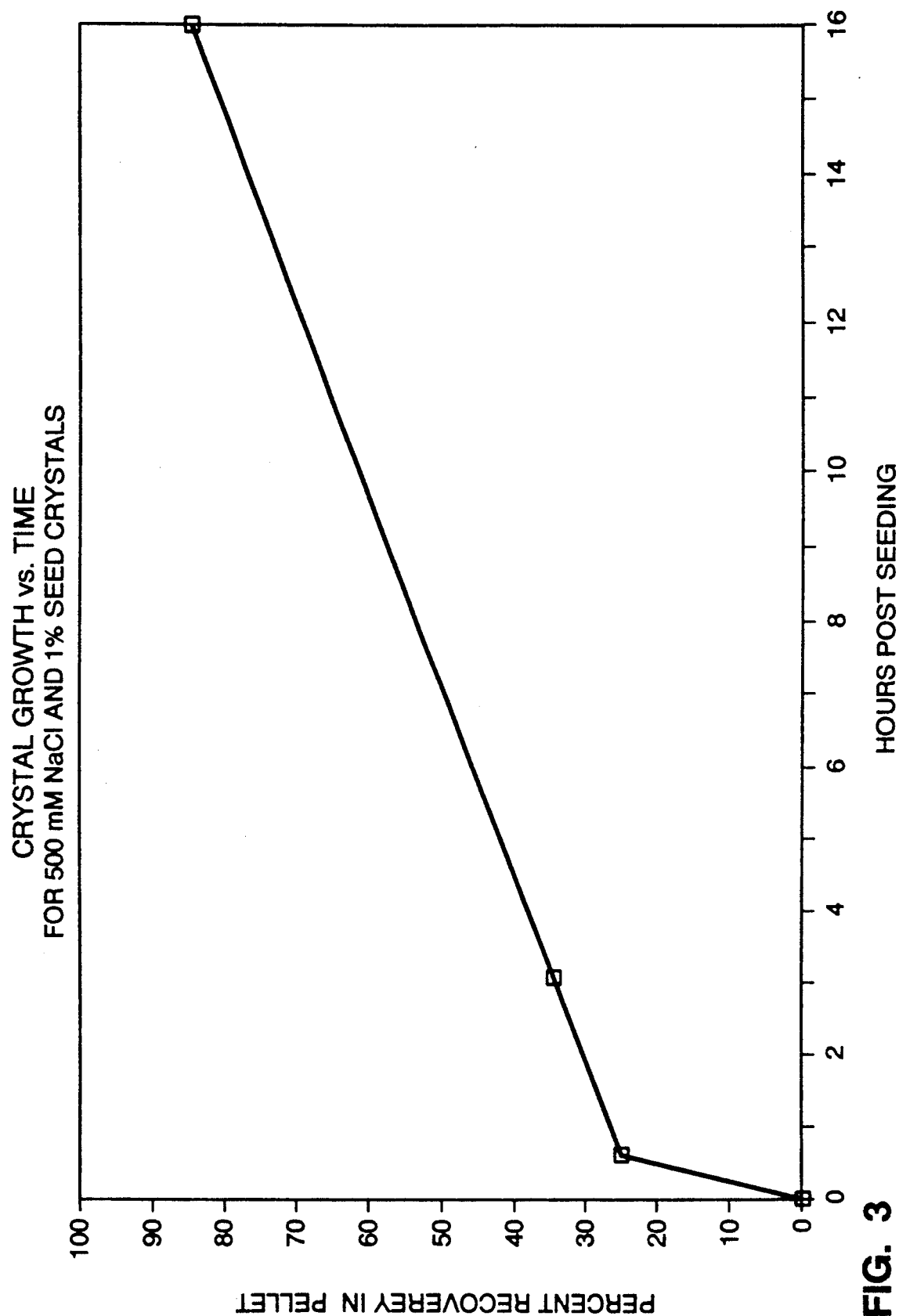
FIG. 3 is a graph depicting the dependence of subtilisin crystal growth in sodium chloride as a function of time.

FIG. 3 illustrates a typical crystallization versus time curve for subtilisin crystallized from a concentrated solution containing about 80 g/l subtilisin, where sodium chloride was added to the concentrated solution as the precipitating salt and where seed crystals were employed. The amount of additional crystal growth after about 16 hours was insubstantial.

Once crystallization is essentially complete, conventional crystal recovery techniques may be used. Thus, product may be recovered from the crystal containing slurry by centrifugation, sedimentation, or filtration. Alternatively, the slurry may be used as a feed to a process for making a solid product.

Two well-known techniques amenable to large scale recovery of product are solid-bowl centrifugation and filtration in a plate-and-frame filter press. In both techniques, the crystal slurry is first diluted with water to reduce viscosity and enhance separation from the mother liquor. In the centrifugation process, the crystals are collected as a dense cake within the bowl and the cake is then washed by resuspending it in water and recentrifuging. The resulting cake is typically redissolved in a formulation including propylene glycol, sodium formate, and water to provide the subtilisin in a desirable liquid product form.

In the filter press recovery process, a filter aid is first added to the diluted crystal slurry and this mixture is pumped to a precoated plate-and-frame filter press. The crystal-free mother liquor filtrate is rejected. Several volumes of water or buffer can then be pumped through the press thereby efficiently washing the crystals under approximately plug-flow conditions. At high enough flow rates of wash buffer, the amount of enzymatic activity lost is insignificant due to the low solubility (3–8 g/l) of the protease crystals in water. The crystalline enzyme is recovered with a buffer containing propylene glycol, sodium formate, and water. These chemicals, in combination with efficient washing of the crystal cake, have been found to result in very low microorganism loads in the product.

The following examples are given by way of illustration and in no way should be construed as limiting the subject matter disclosed and claimed.

EXAMPLE 1

A mixture of *B. amyloliquifaciens* subtilisin produced by fermentation of *B. subtilis* was filtered to remove cells and suspended solids to produce a partially concentrated broth or solution of subtilisin, which was desalted on a 900 ml Pharmacia "Sephadex" G-25 column and equilibrated with 14 mM (0.206%) calcium chloride dihydrate. The original broth had a conductivity of 44 mS/cm but after desalting, the conductivity dropped to 3.9 mS/cm. The solution was diluted with water from 15.8 g/l to 12.3 g/l subtilisin, then concentrated in Amicon stirred UF cells to produce concentrates containing about 65 g/l of subtilisin enzyme. One ml samples of the concentrate were combined matrixwise with varying quantities of sodium chloride and calcium chloride in microfuge tubes placed in an ice bath, and allowed to sit without agitation.

The microfuge tubes containing the crystallized subtilisin were spun in a clinical centrifuge at about 5000 rpm for 4–5 minutes and the supernatant decanted with a Pasteur Pipette. The pellets were taken up first in 100% propylene glycol and then enough 14 mM aqueous $CaCl_2$ was added to give 20% propylene glycol overall. Supernatant and pellet volumes were measured by weight.

The results are reported in the following table.

TABLE

Pellet recoveries of crystalline subtilisin from a solution containing 65 g/l subtilisin using NaCl or $CaCl_2$ precipitant.

| Precipitant | Precipitant Concentration (mM) | Percent of Total Subtilisin Recovered In Pellet |
|---|---|---|
| NaCl | 0 | — |
|  | 50 | — |
|  | 100 | 5.8 |
|  | 200 | 26.2 |
|  | 250 | 38.0 |
|  | 500 | 69.4 |
|  | 1000 | 66.0 |
|  | 1500 | 13.9 |
| $CaCl_2$ | 0 | — |
|  | 50 | — |
|  | 100 | 24.3 |
|  | 200 | 36.9 |
|  | 250 | 61.8 |
|  | 400 | 15.3 |
|  | 500 | 12.4 |

In the above Table, a dash (-) indicates no significant recovery of a crystallization product.

The above example demonstrates that the optical concentrations of sodium chloride and calcium chloride in this case are about 500 mM and about 250 mM, respectively.

EXAMPLE 2

A variant enzyme of the *B. amyloliquilofaciens* protease (made by substituting the amino acid leucine at position 217 in the subtilisin molecule) was fermented, filtered, concentrated and crystallized by the same method as in Example 1.

A cell-free solution of the protease was concentrated in this case by ultrafiltration to 69 g/l subtilisin. Varying levels of sodium chloride and natural enzyme seed crystal were added to the concentrate, resulting in the following yields of the engineered enzyme crystals:

| % v/v Seed Added | NaCl (mM) | % Activity Recovered |
|---|---|---|
| 0 | 400 | 41 |
| 1 | 0 | 24 |
| 1 | 200 | 69 |
| 1 | 400 | 78 |

EXAMPLE 3

A subtilisin solution from ultrafiltration was concentrated to 99 g/l. Various halide salts at 400 mM were added to the conventional solution and 1% v/v enzyme crystal seed was added. Resulting crystal recoveries after 6 days incubation at 4° C. were as follows:

| Salt | % Solids @ 1 Day | % Solids @ 6 Days | % Activity Recovered |
|---|---|---|---|
| None | 8 | 16 | 34 |
| NaCl | 23 | 22 | 68 |
| NaI | 25 | 23 | 76 |
| KCl | 27 | 25 | 84 |
| KI | 26 | 25 | 81 |

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A process for the preparation of subtilisin crystals comprising:
   (i) preparing a subtilisin solution by removing cells and suspended solids from a fermentation mixture produced by fermentation of a subtilisin-producing bacterium;
   (ii) forming a concentrated solution by concentrating the subtilisin solution such that the subtilisin is present in a concentration of at least about 40 g/l; and
   (iii) adding a halide salt in an amount effective to cause formation of subtilisin crystals.

2. The process of claim 1 wherein halide salt is added to the fermentation mixture.

3. The process of claim 1 wherein halide salt is added to the subtilisin solution.

4. The process of claim 1 wherein halide salt is added to the concentrated solution.

5. The process of claim 1 wherein the concentrating step (ii) is carried out such that the concentration of subtilisin is at least about 80 g/l.

6. The process of claim 1 wherein the salt is sodium chloride or calcium chloride.

7. The process of claim 4 wherein the salt is sodium chloride and is added to form a solution having from about 400 to about 500 mM of sodium chloride.

8. The process of claim 4 wherein the salt is calcium chloride and is added to form a solution having from about 50 to about 200 mM of calcium chloride.

9. The process of claim 1 further comprising adding seed crystals of subtilisin to the concentrated solution.

10. The process of claim 1 wherein said step (iii) of forming subtilisin crystals is performed at a pH between about 5.2 and about 5.8.

11. The process of claim 1 wherein the bacterium is a bacillus.

12. The process of claim 10 wherein the bacillus is *B. subtilis*.

13. The process of claim 5 wherein the concentration of subtilisin is between about 80 and about 100 g/l.

14. The process of claim 1 wherein the salt is sodium iodide.

15. The process of claim 1 wherein the salt is potassium chloride.

16. The process of claim 1 wherein the salt is potassium iodide.

17. A process for the purification of subtilisin comprising forming a concentrated subtilisin solution having a subtilisin concentration of at leas about 40 g/l and adding a halide salt to a subtilisin solution wherein the amount of halide salt is an amount effective to cause crystallization of subtilisin from the solution.

18. The process of claim 17 wherein the halide salt concentration in the solution is from about 0.01 to about 2 M, and the subtilisin concentration in the solution is at least about 40 g/l.

19. A composition comprising a subtilisin solution having a subtilisin concentration in the solution of at least about 40 g/l, containing a halide salt present in an amount effective to cause crystallization of subtilisin from the solution.

20. A composition according to claim 19 wherein the salt concentration in the solution is from about 0.01 to about 2 M and the subtilisin concentration in the solution is at least about 60 g/l.

* * * * *

UNITED STATES PATENT AND TRADEMARK OFFICE
CERTIFICATE OF CORRECTION

PATENT NO. : 5,041,377
DATED : August 20, 1991
INVENTOR(S) : Todd Becker et al.

It is certified that error appears in the above-identified patent and that said Letters Patent is hereby corrected as shown below:

Column 1, line 40, delete "liter(g/l)" and insert in place thereof --liter (g/l)--:
Column 2, lines 4 and 5, delete "subsaturation" and insert in place thereof --supersaturation--;
Column 3, line 56, delete "occurs" and insert in place thereof --occur--;
Column 5, line 21, delete "is" and insert in place thereof --are-- and line 67, delete "0.8 M" and insert in place thereof --0.18 M--;
Column 8, line 65, delete "optical" and insert in place thereof --optimal--;
Column 9, line 3, delete "amyloliquilofaciens" and insert in place thereof --amyloliquifaciens--;
Column 10, line 39, delete "leas" and insert in place thereof --least--.

Signed and Sealed this

Thirtieth Day of March, 1993

*Attest:*

STEPHEN G. KUNIN

*Attesting Officer*   Acting Commissioner of Patents and Trademarks